US005600444A

United States Patent [19]
Tong

[11] Patent Number: 5,600,444
[45] Date of Patent: Feb. 4, 1997

[54] DETECTING ANALYTE LIGHT ABSORPTION UTILIZING DEGENERATE FOUR WAVE MIXING

[75] Inventor: William G. Tong, San Diego, Calif.

[73] Assignee: San Diego State University Foundation, San Diego, Calif.

[21] Appl. No.: 527,289

[22] Filed: Sep. 12, 1995

Related U.S. Application Data

[63] Continuation of Ser. No. 181,676, Jan. 13, 1994, abandoned.

[51] Int. Cl.$^6$ ............................................. G01N 21/00
[52] U.S. Cl. ....................... 356/432; 356/436; 356/439
[58] Field of Search ............................. 356/432, 433, 356/434, 436, 437, 440, 491, 442, 335–342, 345, 346

[56] References Cited

U.S. PATENT DOCUMENTS

| | | | |
|---|---|---|---|
| 4,284,354 | 8/1981 | Liao | 356/301 |
| 4,355,897 | 10/1982 | Kaye | 356/338 |
| 4,540,283 | 9/1985 | Bachalo | 356/336 |
| 4,662,642 | 11/1986 | Bajard et al. | 356/335 |
| 4,854,705 | 8/1989 | Bachalo | 356/336 |
| 5,166,507 | 11/1992 | Davis et al. | 356/121 |

OTHER PUBLICATIONS

Wu and Tong, "Forward–Scattering Degenerate Four–Wave Mixing As a Simple Sub–Attomole–Sensitive Nonlinear Laser Analytical Spectrometric Method," Anal. Chem. 1993, 65, 112–117.

Wu and Tong, "Laser Analytical Spectrometry Based on Optical Phase Conjugation by Degenerate Four–Wave Mixing in a Flowing Liquid Analyte Cell," Anal. Chem. 1989, 61, 998.

Wu and Tong, "Trace–Concentration Detection of Cobalt in a Liquid Flow Cell By Degenerate Four–Wave Mixing Using Low–Power Off–Resonant Laser Excitation," Anal. Chem. 1991, 63, 1943–1947.

*Primary Examiner*—Frank Gonzalez
*Assistant Examiner*—Jason D. Eisenberg
*Attorney, Agent, or Firm*—Fish & Richardson P.C.

[57] ABSTRACT

A method and apparatus using either two or three input laser beams in a nonlinear degenerate four-wave mixing arrangement for ultrasensative analytical measurements of an analyte. In accordance with a first embodiment of the present invention, a two input beam F-D4WM arrangement is used to generate two phase conjugate signal beams. The input beams are narrowly focused to intersect within a very small volume of an analyte. The analyte may be in any physical state (e.g., liquid, solid, or gas). The intensity of the signal beam is used to detect trace concentrations of particular substances. The beam spot of each of the input beams can be focused to less than 34 μm, thus allowing the present invention to directly focus the input beams within a capillary tube of a HPCE or a column of a HPLC system. In accordance with the second embodiment of the present invention, the input laser beams of a F-D4WM method are directed to points on a lens by immobilized fiber optic cables. In accordance with a third embodiment of the present invention, a three input beam B-D4WM method is used in which the three input laser beams are directed by an immobilized fiber optic cable.

38 Claims, 11 Drawing Sheets

$$\Delta K = K_2 + K_3 - 2K_1$$

$$\Delta K = K_1 + K_4 - 2K_2$$

DETECTING ANALYTE LIGHT ABSORPTION UTILIZING DEGENERATE FOUR WAVE MIXING

This is a continuation of application Ser. No. 08/181,676, filed Jan. 13, 1994, now abandoned.

BACKGROUND OF THE INVENTION

1. Field of the Invention

This invention relates to a method and apparatus for nonlinear laser spectroscopy, and more particularly, to a method and apparatus using two or three input laser beams in a nonlinear four-wave mixing setup for ultrasensative analytical measurements of an analyte.

2. Description of Related Art

Research has taken place with regard to degenerate four-wave mixing (D4WM) techniques using a "backward-scattering" degenerate four-wave mixing (B-D4WM) optical setup for analytical measurements in discharge atomizers (see Tong, W. G., Chen, D. A., Appl. Spectrosc. 1987, 41, 586–590), flame atomizers (see Tong, W. G., Andrews, J. M., Wu, Z., Anal Chem. 1987, 59, 896–899), and room-temperature flow cells (see Wu, Z., Tong, W. G., Anal Chem. 1989, 61, 998–1001). In particular, the inventor of the present invention has described the use of B-D4WM to detect trace-concentrations of an analyte, such as eosin B dissolved in ethanol. In such an application of B-D4WM, two counter-propagating pump beams and a probe beam are mixed inside a nonlinear medium, and a phase-conjugate signal beam is generated via one of the four-wave mixing mechanisms. FIG. 1 illustrates the set-up used for detecting trace-concentrations in this manner. A laser beam 101 is generated by an argon ion laser. The laser beam is split by a first beam splitter 103, such that a first portion of the laser beam 101 forms the forward pump beam 107, and a second portion of the laser beam 101 forms the backward pump beam 109. The forward pump beam 107 is reflected by a reflector 111 which directs the forward bump beam toward an analyte cell 113. The analyte cell contains a volume of an analyte. The backward pump beam 109 is reflected by a second reflector 115 toward the analyte cell in the opposite direction from the forward pump beam 107. A portion 117 of the laser beam that passes through the first beam splitter 103 is reflected by the second beam splitter 105. The second portion of the laser beam is the probe beam 117. The probe beam 117 is reflected by the second beam splitter 105 through an amplitude modulation device 118 (such as a mechanical chopper), an aperture 120, a third beam splitter 123, and a lens 122, to a reflector 119. The reflector directs the beam 117 to the point in the analyte cell 113 to which both the forward pump beam and the backward pump beam 109 are directed. Generation of an optical phase conjugate beam 121 by D4WM in an absorbing liquid sample of an analyte contained within the analyte cell 113 results from formation of spatial gratings due to a thermally induced refractive index change in the nonlinear medium of the sample. The phase conjugate reflectivity can be described as:

$$R = I_s/I_p = f^2 Q^2 I_f I_b \exp(-\alpha L)[1-\exp(-\alpha L/\cos \Theta)]^2 G(t_D)$$

Where:

$I_s$, $i_p$, $I_f$, and $I_b$=the beam intensity of the conjugate signal beam 121, probe beam 117, forward pump beam 107, and backward pump beam 109, respectively;

f=the fraction of absorbed light energy converted into heat, and is inversely proportional to the quantum efficiency of fluorescence of the analyte;

α=the absorption coefficient;

L=the sample path length;

Θ=is the angle between the forward pump beam 107 and the probe beams 117;

$Q = [2n\, (dn/dt)_p]/(\lambda \rho_o C_p)$;

$(dn/dt)_p$=the change of refractive index due to temperature change at constant pressure, $\rho_0$=the equilibrium solvent density;

$C_p$=the specific heat at constant pressure,;

λ=the wavelength of the excitation laser source;

$G(t_D)$=thermal grating evolution and depends on the thermalization time and thermal diffusion time constant for the analyte molecules in the solution.

The above equation can be simplified to:

$$I_s \sim Q^2 I^3 (\alpha L/\cos \Theta)^2$$

by assuming that the absorption of the solution is small and the sample path length is short. Therefore, according to this formula, the intensity of the optical phase conjugate signal is proportional to the square of the absorption coefficient, and hence to the analyte concentration. Thus, by accurately measuring the intensity of the optical phase conjugate signal generated by incident light defracted off the spatial gratings generated in the sample in the analyte cell 113, the concentration of the analyte can be determined.

The signal beam 121 is transmitted back along the path of the input beam 117, and is reflected by the third beam splitter 123 toward an aperture 125, a filter 127, and a photomultiplier tube 129. The output of the photomultiplier tube is coupled to a lock-in amplifier 131, which filters out amplitude variations that occur at frequencies other than the frequency of the chopper 118 and out of phase with the chopper. The output of the lock-in amplifier 131 is then coupled to a computer 135 comprising an analog to digital converter. The computer 135 processes intensity information to determine the concentration of the analyte that was present in the sample cell 113.

This method for measuring concentrations has a detection limitation that makes it useful for detecting trace amounts of a substance, such as eosin B which is used in many areas, including protein labeling, and artificial food coloring. However, the amount of analyte that must be provided within the sample cell of such detectors is greater than is desireable in many circumstances. For example, when used with a capillary electrophoresis system, the laser beams are very difficult to focus within the very small confines of capillary tubes typically used. Furthermore, the physical set-up is difficult to align due to the fact that three beams which reflect off of five surfaces must be aligned to cause a phase conjugate signal to be generated. Furthermore, it would be desireable to reduce the laser power requirements and even further decrease the mass detection limitations of the system. Still further, it would be desirable for the laser probe volume to be reduced with shorter analyte absorption path length.

The present invention provides a method and apparatus which has lower mass detection limitations than the prior art, requires less laser power, is much easier to align, provides a means by which the laser beams used can be focused and mixed with a single lens within a sufficiently small area to allow detection directly within the capillary tube of a capillary electrophoresis system, and allows virtually any substance to be analyzed.

SUMMARY OF THE INVENTION

The present invention is a method and apparatus using either two or three input laser beams in a nonlinear degenerate four-wave mixing arrangement for ultrasensitive analytical measurements of an analyte. In accordance with a first embodiment of the present invention, a two input beam forward-scattering degenerate four-wave mixing arrangement is used to generate two phase conjugate signal beams. Constructive interference between the two input beams creates a dynamic grating at a point at which the two input beams intersect. In accordance with the first embodiment of the present invention, the input beams are narrowly focused to intersect within a very small volume of an analyte. The analyte may be in any physical state (e.g., liquid, solid, or gas). The signal beams are then generated by the scattering of the input beams off the grating. The intensity of each phase conjugate signal beam is proportional to the square of the absorption coefficient of the analyte present at the point at which the two input beams are focused, and to the cube of the total intensity of the sum of the two input beams. The absorption coefficient of the analyte may be used to detect trace concentrations of particular substances in known fashion. Thus, by monitoring the intensity of a signal beam generated by the interference pattern setup when two input beams intersect within an analyte, ultratrace concentrations of substances of interest may be detected.

The use of two input beams in accordance with the first embodiment of the present invention allows a single lens to be used to focus and mix the input beams simultaneously. Thus, the beam spot of each of the input beams can be focused to less than 34 µm. Such small beam spots allow the present invention to directly focus the input beams within a standard component of an analysis system, such as a capillary tube of a high power/high performance capillary electrophoresis (HPCE), a column of a high performance liquid chromatography (HPLC) system, or to directly probe a small location inside a gas-phase atomizer such as flame, dc plasma, graphite furnace, inductively coupled plasma for diagnostic studies with high spatial resolution. Due to the fact that the first embodiment of the present invention uses only two input beams, the first embodiment of the present invention is far easier to align than prior art system which require three input beams.

Furthermore, since the present invention does not rely on fluorescent properties of the analyte, any substance that absorbs light at the wavelength of the laser used can be directly detected. Furthermore, even substances that do not absorb light at convenient wavelengths (such as amino acids, which absorb light only at ultraviolet wavelengths) can be indirectly detected. In accordance with an indirect method of detection, a liquid is selected for having desirable D4WM parameters including absorption coefficient, since the absorption coefficient is the parameter that is to be used to determine the presence of the liquid. The liquid then yields a positive baseline value. The sample to be detected is then injected into the system. The presence of the sample can then be detected to a very precise degree by the change in the measured absorption coefficient of the liquid. Therefore, in accordance with the present invention, trace concentrations of virtually any substance may be detected, without the use of a laser emitting light at a wavelength suited to that particular substance, since the liquid is the signal generating medium. Furthermore, in accordance with the present invention, an inexpensive diode laser may be used to generate the input laser beams, thus reducing both the cost and the size of the present invention. The use of low-power diode lasers, HeNe lasers or other compact inexpensive lasers is possible in accordance with the present invention because F-D4WM requires significantly less laser power and offers easier mixing and handling of less than perfect laser beams. For example, laser beams that are poorly columnated or which are highly divergent are refocused in accordance with the two-input-beam embodiment of the present invention.

In accordance with the second embodiment of the present invention, the input laser beams and the signal beam of a forward-scattering degenerate four-wave mixing method are carried by fiber optic cables. The fiber optic cables are secured to a substrate or mount such that they are immobilized with respect to the other components of the invention, such as the lens, apertures and a sample cell. Thus, the alignment of the system is preset and needs no further adjustment.

In accordance with a third embodiment of the present invention, a three input beam backward degenerate four-wave mixing method is used in which the two input laser beams are directed by fiber optic cables from the laser light source to opposite sides of a sample cell, and the third input beam is directed by a fiber optic cable from the laser light source to the sample cell through a beam splitter and a lens. The signal beam is also directed via fiber optic cable toward the detector. Each of the fiber optic cables is secured to a substrate such that the fiber optic cable is immobilized with respect to each other component of the system. The use of fiber optic cables to direct the laser beams of a three input beam system is of particular value due to the difficulties encountered in aligning such three beam systems.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 3 graphically illustrates the relationship between the total power of the sum of the input beams and signal beam power, using actual data points observed from the embodiment of the present invention illustrated in FIG. 2a.

FIG. 6 is a photograph of the four laser spots formed by the embodiment the present invention illustrated in FIG. 2a.

Figures are not to scale. Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Physical Configuration of the Preferred Embodiment

Figure 2A:
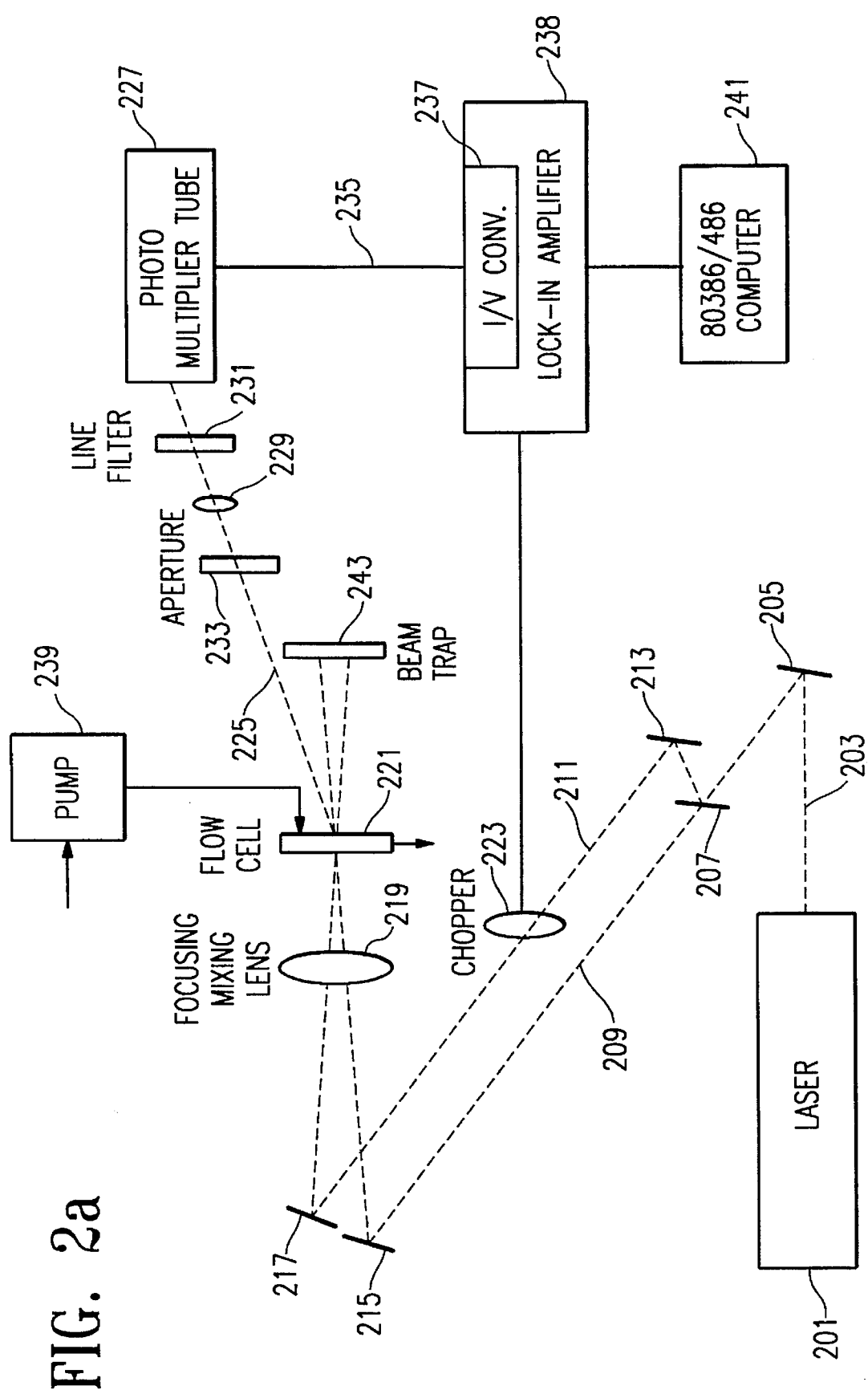
FIG. 2a is a schematic diagram of a two-input-beam forward-scattering degenerate four-wave mixing arrangement in accordance with the preferred embodiment of the present invention.

FIG. 2a shows a schematic diagram of a two-input-beam forward-scattering degenerate four-wave mixing F-D4WM arrangement in accordance with the preferred embodiment of the present invention. It should be understood that the particular arrangement of reflectors and beam splitters is provided only as an exemplar, and is not intended to limit the scope of the present invention.

The present invention includes an excitation light source 201, which is preferably a compact diode laser, such as is commonly known. Alternatively, a helium-neon laser, a continuous-wave argon ion laser or a Nd:YAG laser may be used. A laser beam 203 output by the light source 201 is preferably reflected by a reflector 205 and split by a beam splitter 207 to form a first 209 and a second 211 input beam. The second input beam 211 is reflected by a second reflector 213 such that the first 209 and second 211 input beams are preferably generally parallel. In accordance with the illustrated embodiment of the present invention, the intensity $I_1$, of the first input beam 209 with respect to the intensity $I_2$ of the second input beam 211 arriving at the sample cell, $I_1:I_2$, is approximately 7:3 to generate the signal in one direction only. The preferred ratio is 1:1 to generate two signal beams.

In the preferred embodiment, a third reflector 215 and a fourth reflector 217 redirect the first input beam 209 and the second input beam 211, respectively, toward a single 100-mm focusing lens 219. The focusing lens 219 preferably focuses and-mixes both input beams 209, 211. A sample cell 221 is placed at the lens' focal point. The diameter of both the first input beam spot and the second input beam spot on the sample cell 221 is approximately 34 μm in the preferred embodiment. The first input beam 209 and the second input beam 211 intersect inside the sample cell 221 with an intersect angle of approximately 1.5° or less in the preferred embodiment of the present invention. The small input beam spots allow the present invention to interface directly with systems in which an analyte is available in a small volume, such as the capillary tube of a high power/high performance capillary electrophoresis system (HPCE), the column of a high performance liquid chromatography (HPLC) system, or to directly probe a small volume inside a gas-phase atomizer such as flame, dc plasma, graphite furnace, inductively coupled plasma, with high spatial resolution in diagnostic studies.

In order to optimize the signal strength of a phase-conjugate signal which is generated, the difference in path lengths (or distances traveled) for first input beam 209 and the second input beam 211 are preferably kept to less than the coherence length of the laser. A device for amplitude modulating the second input beam 211, such as a mechanical light chopper 223 (for example, Model 03-OC4000, manufactured and distributed by Photon Technology International Inc., Princeton, N.J.), or any solid state electronic light intensity modulation device, is used. A phase-conjugate signal beam 225 generated in the sample cell 221 is directed to a detector 227, such as a photomultiplier tube (e.g., Model R928, manufactured and distributed by Hamamatsu Corp., Middlesex, N.J.) after passing through a lens 229 preferably having a 250-mm focal length and preferably a filter 231 which in the preferred embodiment is a 514.5 nm laser-line filter when using an argon ion laser. A small aperture 233 is preferably disposed in front of the detector 227 to minimize background noise due to the scattering of the two input beams 209 and 211.

The electrical output signal 235 of the detector 227 is then preferably coupled to a current-to-voltage converter 237, the output of which is preferably monitored by a lock-in amplifier (otherwise known as phase sensitive amplifier) 238 (such as Model 5207, manufactured and distributed by Princeton Applied Research, Princeton, N.J.). The output from the detector 227 may also be coupled to other processor components 241, such as a strip-chart recorder, personal computer including an analog to digital converter, or any other such processing device. Control of the present invention may be performed by the same computer used to control a HPCE, HPLC, or atomizer system with which the present invention is being used.

The sample cell 221 is preferably the capillary of an HPCE system, the column of an HPLC system, or a gas-phase atomizer system (e.g., flame, dc plasma, ICP plasma, graphite furnace). However, a rectangular glass flow cell with approximately a 0.1-mm optical path length (such as a Type 48, manufactured and distributed by Starna Cells, Inc., Atascadero, Calif.) may be used to measure an analyte for other purposes. Naturally, the sample cell 221 may take any form which can hold a volume of analyte which is at least equal to the spot volume of the focused input beams 209, 211, and which allows the input beams 209, 211 to enter and the signal beam 225 to exit without excessive attenuation. Furthermore, the analyte in the sample cell 221 may be any substance in any phase (i.e., liquid, solid, or gaseous), such as eosin B dissolved in ethanol and iodine in carbon tetrachloride. The present invention is capable of analyzing solids and gases, as well as liquids.

An analyte solution is preferably delivered to the sample cell 221 in accordance with the system with which the present invention is being used. For example, the analyte is delivered by electrophoresis in an HPCE system or a pump in a HPLC system. Alternatively, a pump, such as a peristaltic pump 239 may be used to deliver the analyte to the sample cell 221.

After the two input beams 209, 211 pass through the sample cell 221, they are blocked by a beam trap 243, and the signal beam 225 is easily separated and directed toward the detector 227. An analyte solution with a relatively high concentration (e.g., $5 \times 10^{-6}$M eosin B) is preferably used as an "alignment solution" to optimize the optical alignment. In accordance with the preferred embodiment of the present invention, a micromolar-level solution can generate a strong signal that is visible to the naked eye, thus allowing simple alignment of the present invention. Signal optimization is performed simply by adjusting the mirrors and the lenses, and by carefully adjusting the position of the sample cell 221 so that the sample cell 221 is at the focal point of the wave-mixing lens, while observing the strength of the visible signal spot on a card (or on a photodetector for trace-concentration analytes). Of course, any other means for determining the maximum strength of the signal beam 225 while adjusting the alignment of the system would be equally acceptable. For example, a self-adjusting system using feedback from the lock-in amplifier 238 might be used to determine the optimum alignment of the system. Once the optical alignment is optimized, the alignment and the signal remain very stable and different analyte solutions could be flowed through and analyzed without any further adjustments.

Figure 2B:
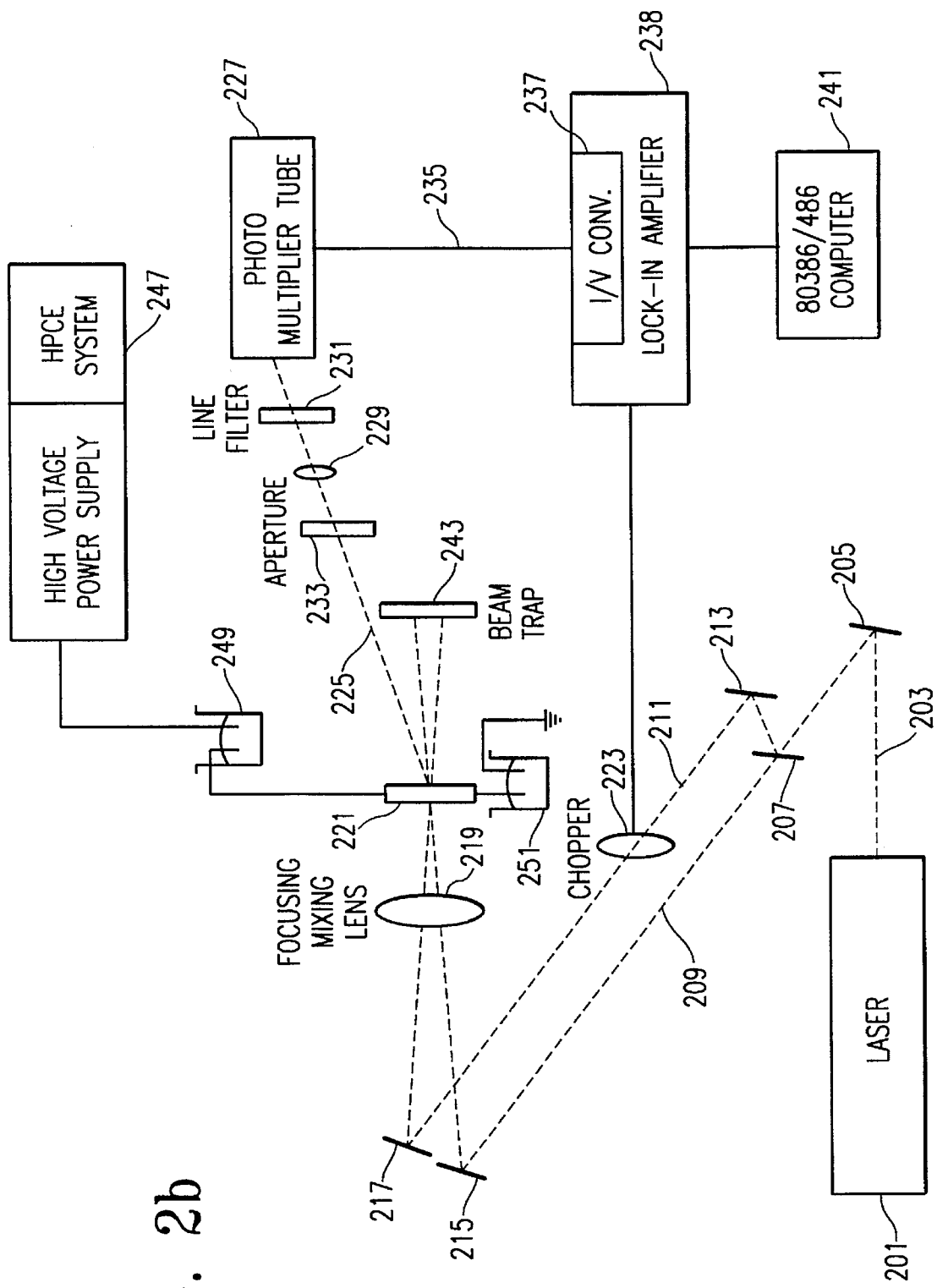
FIG. 2b is a schematic diagram of a two-input-beam forward-scattering degenerate four-wave mixing arrangement coupled to a high performance capillary electrophoresis system.

FIG. 2b illustrates the two-input-beam embodiment of the present invention coupled to the capillary tube of a HPCE system. The sample cell 221 is part of the capillary tube of the HPCE system. One end of the sample cell draws from a positive pool 249. The other end of the sample cell discharges into a negatively charged pool 251. A high voltage source is coupled to, and controlled by, the HPCE system controller 247.

Figure 2C:
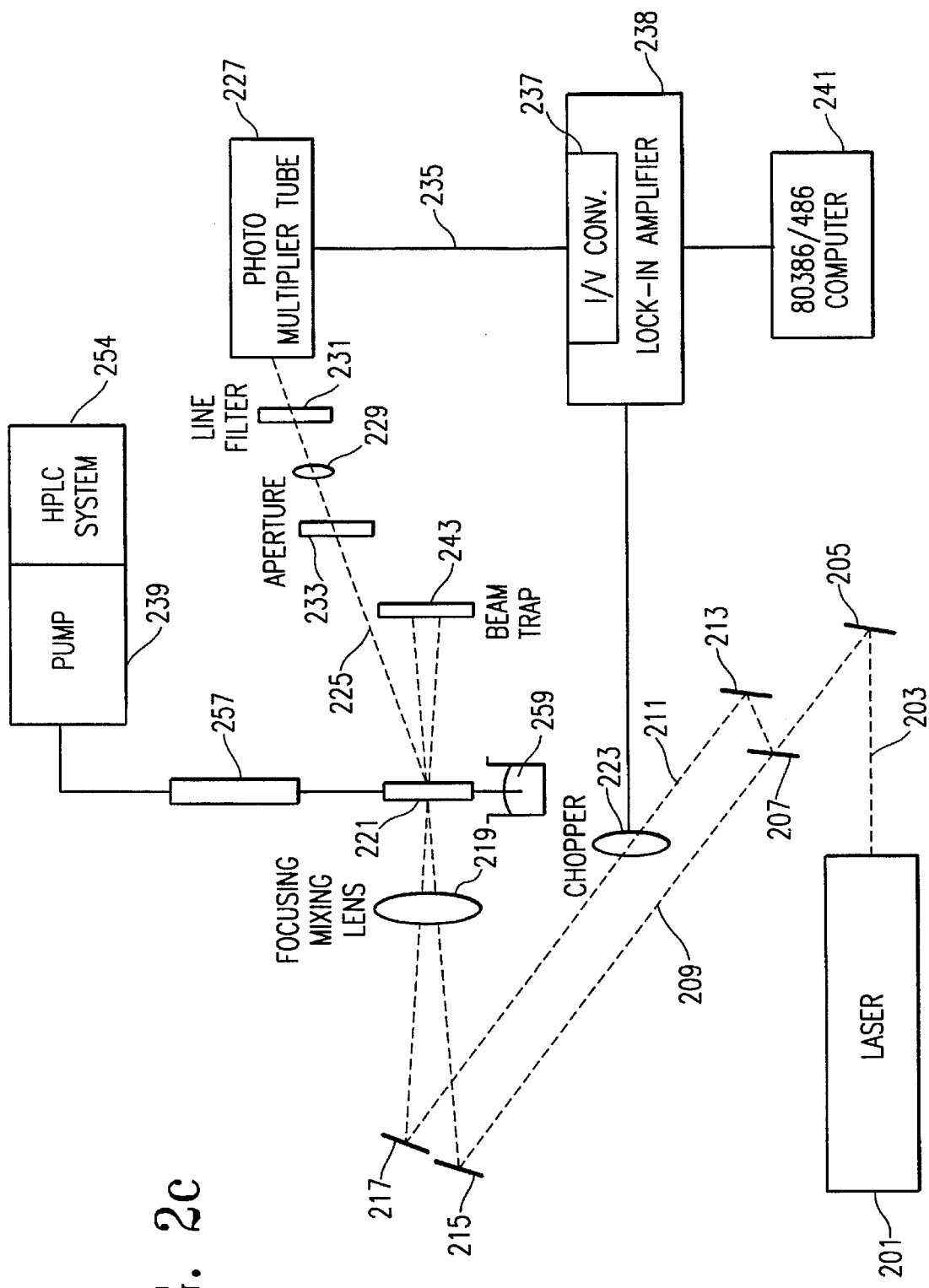
FIG. 2c is a schematic diagram of a two-input-beam forward-scattering degenerate four-wave mixing arrangement coupled to a high performance liquid chromatography system.

FIG. 2c illustrates the two-input-beam embodiment of the present invention coupled to a column 257 of a HPLC system. The sample cell 221 is coupled at one end to the column 257, and at the other end to a waste pool 259. A pump is coupled to, and controlled by, a HPLC system controller 255.

Figure 2D:
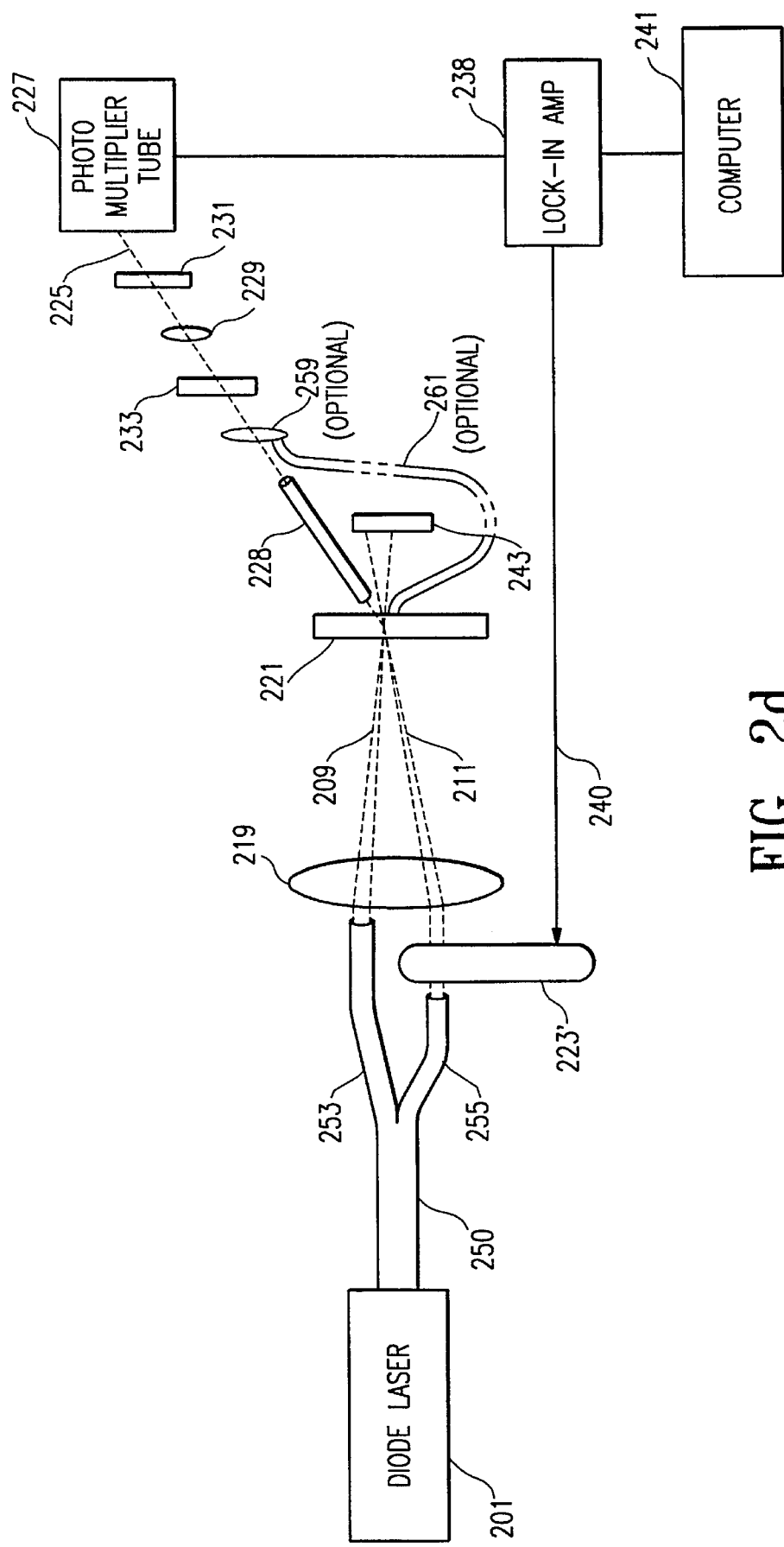
FIG. 2d is an illustration of an alternative embodiment of the arrangement shown in FIG. 2a in which the laser beams are each transmitted through a fiber optic cable.

In an alternative embodiment of the present invention illustrated in FIG. 2d, the laser beams 209, 211, 225 are each transmitted through a fiber optic cable 250. In such embodiments, transmission of laser light through air is preferably minimized. The fiber optic cable may be prealigned and bound to a substrate to prevent misalignment. In such an embodiment, the output of the laser source 201 is coupled directly to the fiber optic cable 250 in known fashion. The fiber optic cable is split in two sections 253, 255 in known fashion, thus dividing the beam into the first input beam 209 and the second input beam 211. The second section of fiber optic cable 255 is preferably coupled to an amplitude modulation device 223', such as a well known mechanical chopper, or any solid state electronic light intensity modulation device or an electro-optical modulator. Use of an electronic circuit for modulating the second input beam 211 allows the system to be produced in a compact package. The output of the first section of fiber optic cable 253 and the output from the modulation circuit 223' are preferably coupled to a lens 219. The lens causes the two input beams 209, 211 to be focused to a fine point within a sample cell 221. The input beams 209, 211 are preferably trapped at the opposite side of sample cell 221 by a beam trap 243. A signal beam 225 is generated within the sample cell 221 and projects outward through an aperture 233, a lens 229, a line filter 231, and into a photomultiplier tube 227. The path from the sample cell 221 to the photomultiplier tube 227 may, in one embodiment of the present invention, be through a fiber optic cable 228. Alternatively, the path may be through air. In one alternative embodiment of the present invention, two signal beams 225, 303 (see FIG. 5a) may be coupled to the photomultiplier tube 227 through a summing lens 259 by fiber optic cable 261, or each signal beam 225 and 303 may be coupled to a separate photomultiplier or photodiode, via air or fiber optic cables and detected by summing or multiplication.

Figure 1:
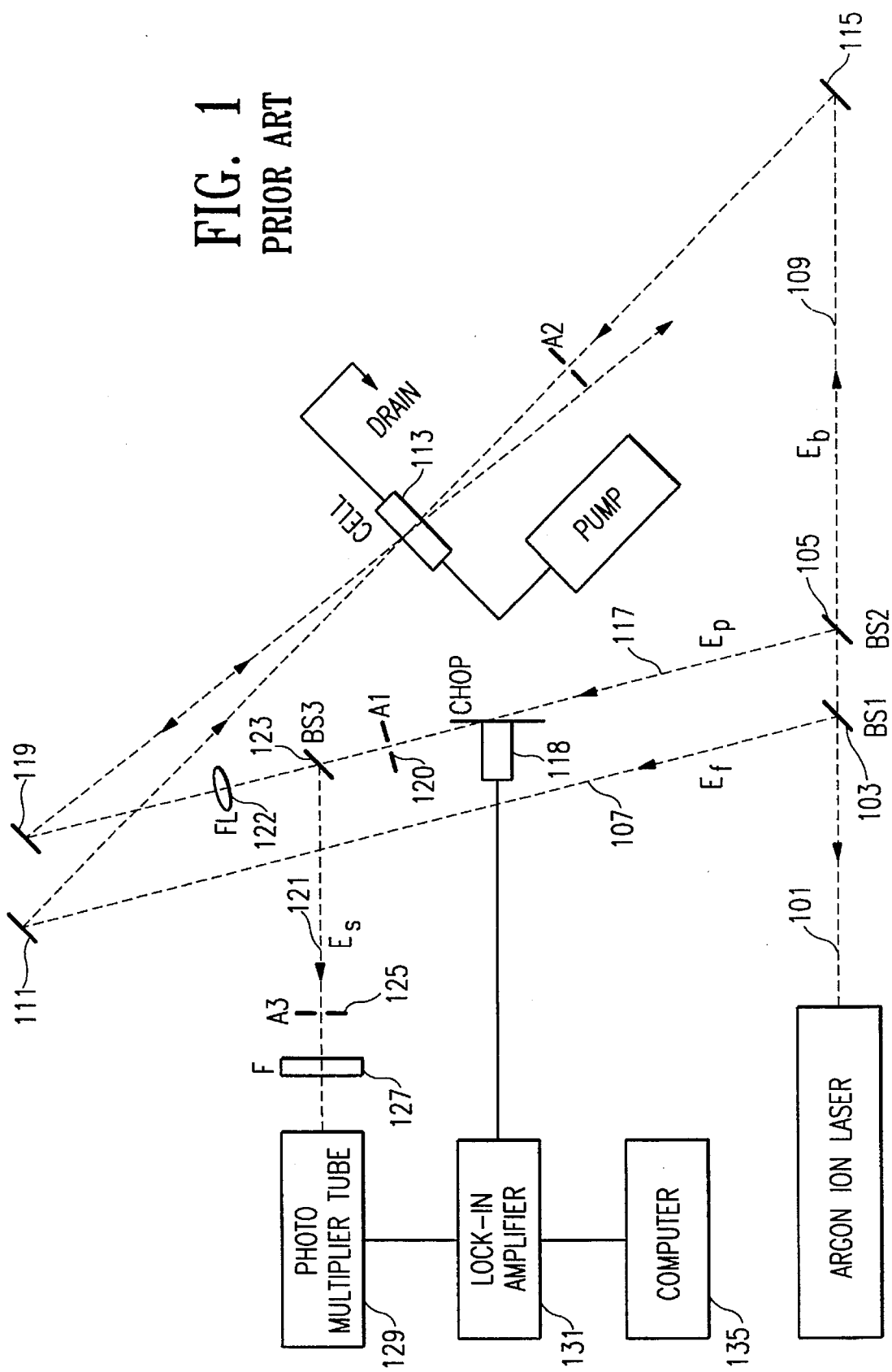
FIG. 1 is a schematic diagram of a prior art three-input-beam backward-scattering degenerate four-wave mixing setup.
Figure 2E:
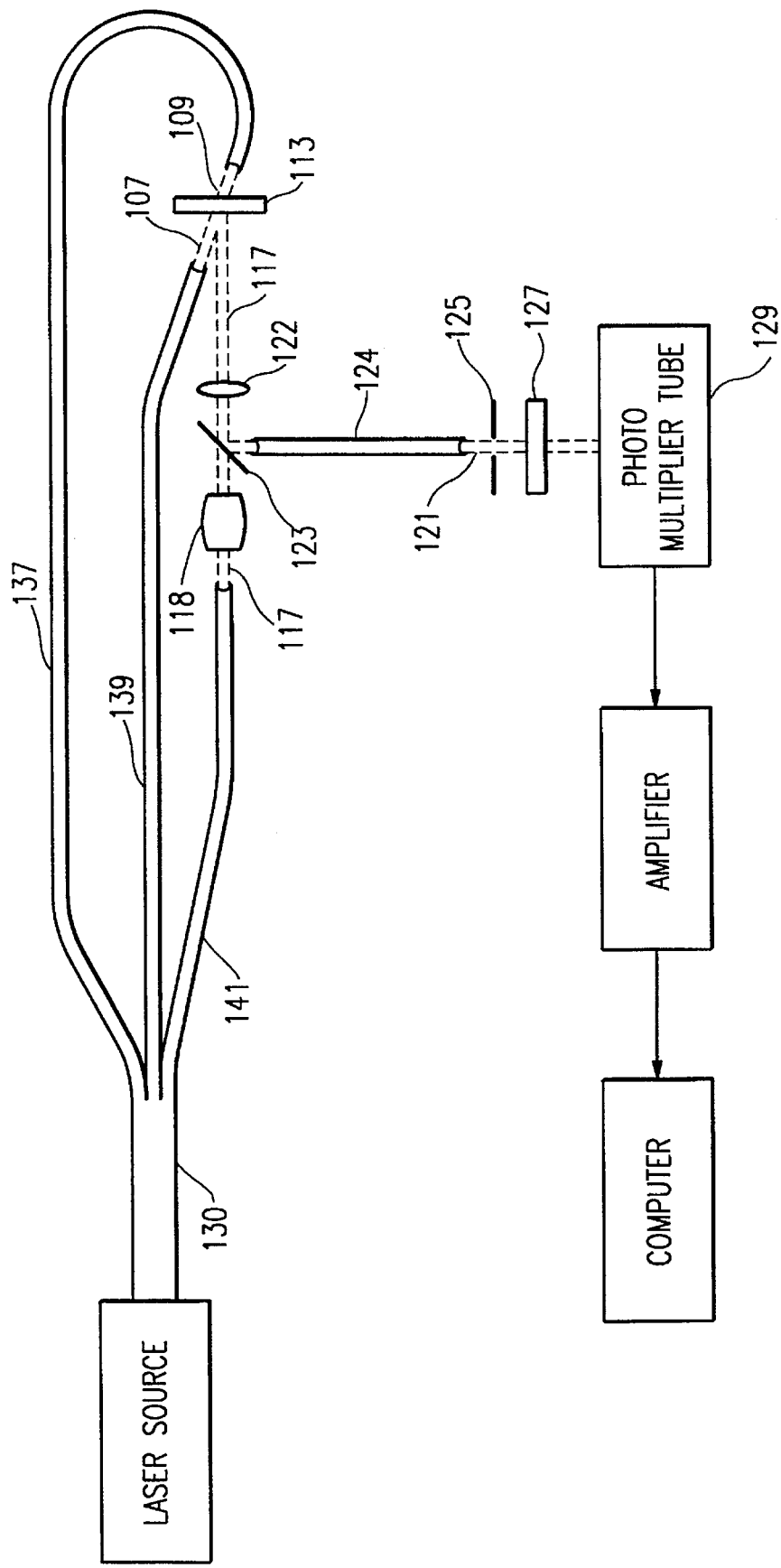
FIG. 2e illustrates a three input beam backward degenerate four-wave mixing arrangement in which fiber optic cables are used to transmit the laser beams.

The use of fiber optic cable to minimize alignment difficulties has particular application to backward D4WM systems, such as the system illustrated in FIG. 1. A system such as that illustrated in FIG. 1 which utilizes fiber optic cables is illustrated in FIG. 2e, a fiber optic cable 130 is divided into three 137, 139, 141 such that the signal is split into three beams 107, 109, 117. One input beam 107 is preferably directed to the sample cell 113 at the appropriate angle by the fiber optic cable 139. The second input beam 117 is directed by the fiber optic cable 141 at a modulation device 118 and a beam splitter 123 which passes the entire input beam 117. The input beam 117 is focused by a lens 122. A signal beam 121 is generated within the sample cell 113 and transmitted along the path that the input beam 117 traverses from the beam splitter 123. Upon striking the beam splitter 123, the signal beam 121 is reflected toward an aperture 125. The signal beam 121 can be directed toward the photodetector via fiber optic cable or through air.

The input beam 109 is transmitted from the laser light source to the sample cell 113 by fiber optic cable 137 at the appropriate angle to counterpropagate the input beam 107 and to cause the desired signal beam 121 to be generated.

Theory Underlying the Present Invention

In an absorbing medium, the phase-conjugate signal beam 225 is generated mostly by thermally induced nonlinear effects. When two coherent beams 209, 211 intersect in the absorbing medium, thermally induced refractive index change is obtained following the absorption of input photons by the analyte species and the subsequent thermalization via rapid radiationless relaxation of optically excited analyte species. Hence, a thermally induced refractive index grating is formed, from which input beams 209, 211 are scattered to produce the phase-conjugate signal beams 225, 303, respectively. The resulting F-D4WM signal intensities, $I_3$ and $I_4$, can be expressed as:

$$I_3 = C I_1^2 I_2 (\lambda^2/\sin^2\theta)[dn/dT]^2 m^2 [\alpha/\kappa]^2$$

$$I_4 C I_1 I_2^2 (\lambda^2/\sin^2\theta)[dn/dT]^2 m^2 [\alpha/\kappa]^2$$

where C is a constant, dn/dT is the temperature coefficient of the refractive index, m is the fringe modulation level, $\alpha$ is the absorption coefficient of the nonlinear analyte medium, and k is the thermal conductivity.

Equations 1 and 2, illustrate several important characteristic properties of the signal beam 225, including quadratic dependence of the signal beam 225 on the intensity $I_1$ of the input beam 209, quadratic dependence of the signal beam 225 on the refractive-index change due to temperature change, and quadratic dependence of the signal beams 225 on the absorption coefficient. Since each of the other variables are known to a high degree of accuracy, the absorption coefficient can be determined to a high degree of accuracy. Determining the absorption coefficient of the solution within the sample cell allows a determination to be made as to the composition of the solution.

Equation 1 also indicates that the intensity $I_3$ of the signal beam 225 has a linear dependence on the intensity $I_2$ of the second input beam 211, a quadratic dependence on the intensity $I_1$ of the first input beam 209, and hence, a cubic dependence on the total intensity $I_t$ of all input beams 209, 211. Similarly, equation 2 shows that the intensity $I_4$ of the signal beam 303 has a linear dependence on the intensity $I_1$ of the first input beam 209, a quadratic dependence on the intensity $I_2$ of the second input beam 211, and hence, a cubic dependence on the total laser intensity $I_t$ of all input beams.

Figure 3:
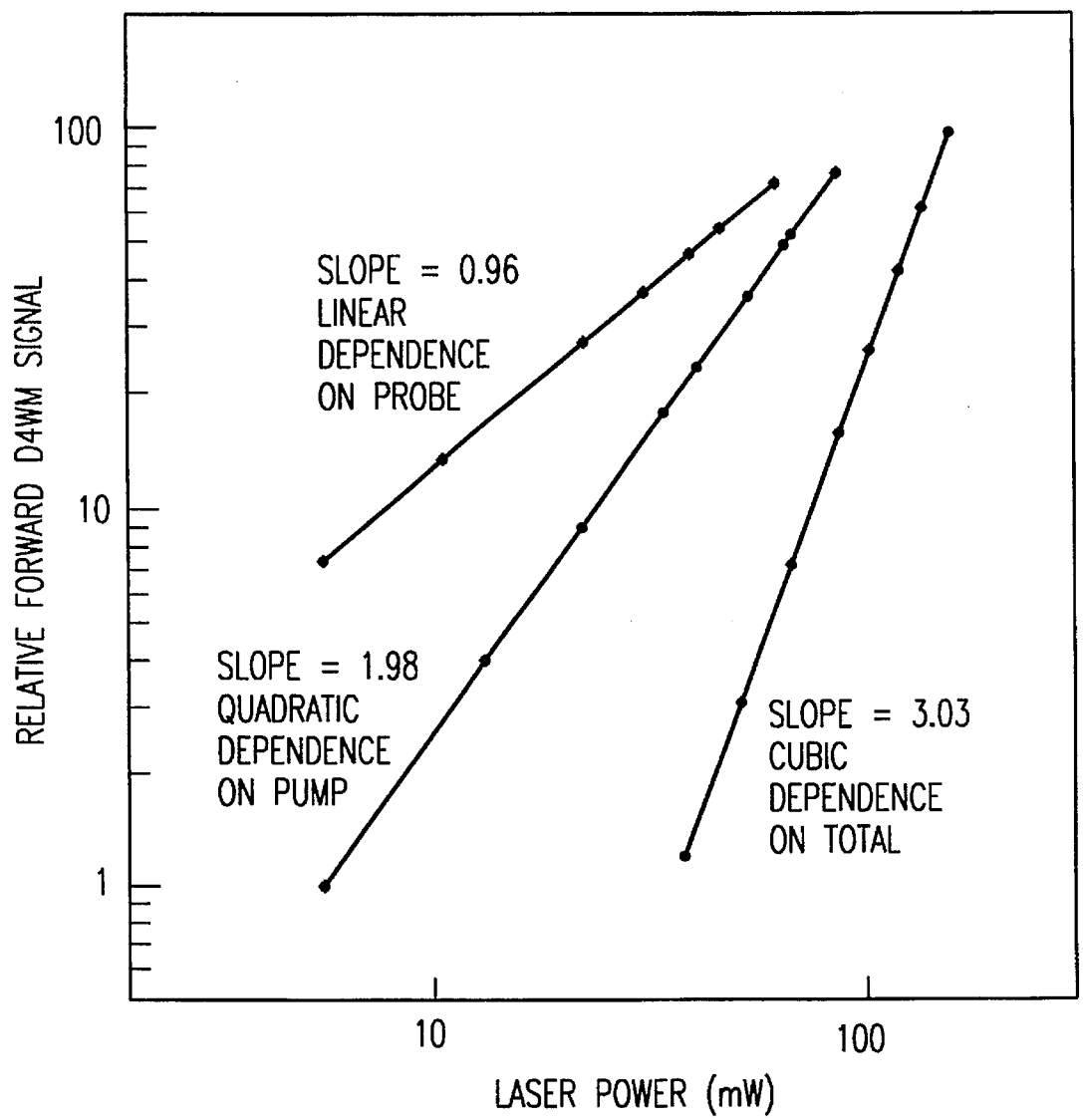

FIG. 3 graphically illustrates the relationship described in equation 1, using actual data points observed from the embodiment of the present invention illustrated in FIG. 2a. Using the embodiment of the present invention shown in FIG. 2a, the signal beam 225 is shown to have a linear dependence (slope=0.96) on the intensity $I_2$ of the input beam 211, a quadratic dependence (slope=1.98) on the intensity $I_1$ of the input beam 209, and a cubic dependence (slope=3.03) on the total input laser intensity $I_t$.

Alternatively, the signal beam 303 has a linear dependence on the intensity $I_1$ of the input beam 209, a quadratic dependence on the intensity $I_2$ of the input beam 211, and a cubic dependence on the total input laser intensity $I_t$. This nonlinear dependence of signal on laser intensity is one of many important characteristics of the F-D4WM method that yield excellent detection sensitivity. For instance, an order of magnitude increase in total laser intensity would result in a 3 orders of magnitude increase for the F-D4WM signal. A good signal to noise ratio is obtained in the present invention despite this non-linear dependence upon the total intensity of the laser beam and the resulting amplification of the fluctuations of intensity of the laser beam, due to (a) the availability of enormous amounts of signal intensity and (b) the signal collection efficiency that is virtually 100% (i.e., signal is a laser beam). In addition, other types of noise, such as background scattering off of optics, increase only linearly with laser power while the signal increases as the cube of the laser power. Hence, the net gain in signal-to-noise ratio is better than that of conventional methods, making it possible for the nonlinear laser method of the present invention to yield excellent S/N and detection limits.

Figure 4:
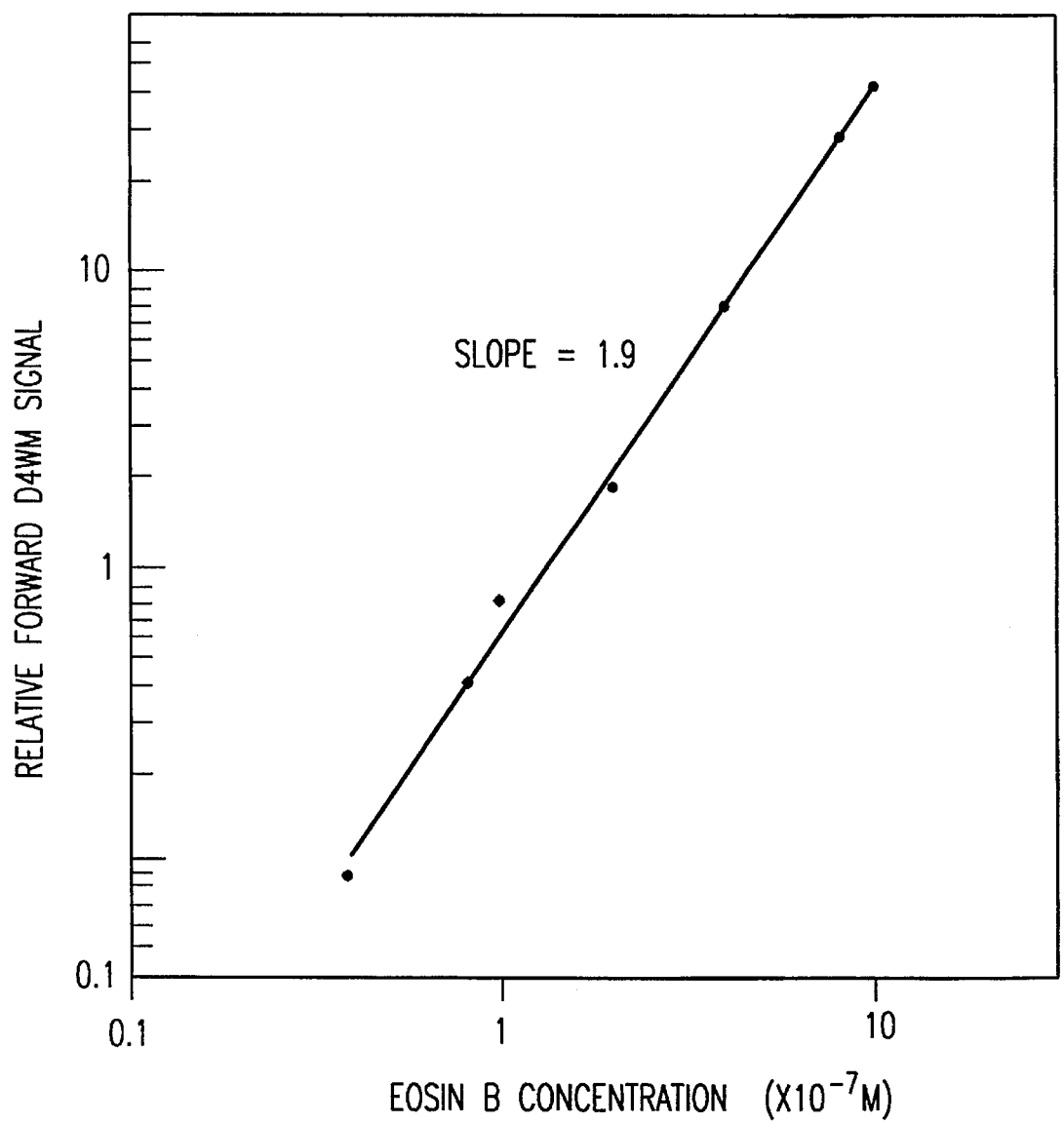
FIG. 4 shows the quadratic dependence of the beam signal on eosin B concentration in a particular application of the present invention.

FIG. 4 shows the quadratic dependence of the beam signal 225 on eosin B concentration in a particular application of the present invention. The quadratic dependence of the beam signal 225 on the eosin B suggested by equations 1 and 2 is shown in FIG. 4. Eosin B is used as an example of an analyte only for convenience. Detection of eosin B is important, since eosin B is currently used in many applications in which detection of trace concentrations of eosin B is important, such as labeling proteins or other molecules and artificial food coloring. However, a major advantage of the present invention is the fact that a very wide range of analytes can be detected, including both fluorescing and non-fluorescing analytes. The only requirement to "direct" detection of an analyte by F-D4WM is the absorption coefficient of the analyte. Even in the case in which a particular sample has poor absorption characteristics (e.g., many amino acids absorb predominately at ultra-violet wavelengths), an "indirect" method of detection may be employed.

In accordance with an indirect method of detection, a liquid is selected for having desirable D4WM characteristics, such as absorption coefficient, since the absorption coefficient is one of the parameters that is to be used to determine the presence of the liquid. Other parameters include third order nonlinear susceptibility, $x^{(3)}$, the refractive index change based on temperature change, dn/dt, and the refractive index, n. The liquid then yields a positive baseline value for the absorption coefficient of the liquid within the sample cell. The sample to be detected is then injected into the system. The presence of the sample can then be detected to a very precise degree by the change in the measured absorption coefficient of the liquid within the sample cell.

The use of such an indirect method for detecting the presence, concentration, or mass of a chemical provide the following benefits: (1) the analysis is applicable to a larger number of substances; (2) a single fixed wavelength laser may be used for any analyte; (3) the wavelength of the laser may be selected to the user's convenience; (4) the maximum absorption wavelength of an analyte may be more than 100 nm away; (5) universal detection of many unlabeled analytes which would otherwise require labeling; (6) neither the solvents nor the analytes require derivitization; and (7) femtomole/attomole-level detection sensitivity is possible.

Figure 5A:
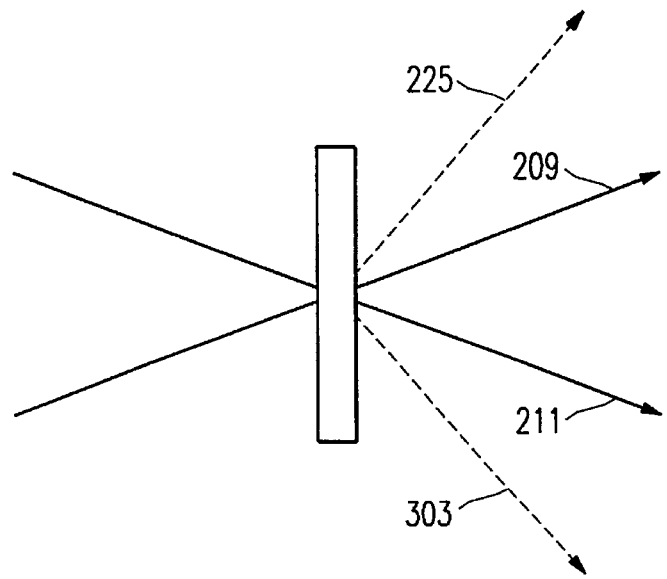
FIG. 5a illustrates a first input beam and a second input beam, which constructively interfere to form a thermal grating, which then scatters the corresponding input beams to generate F-D4WM signal beams.
Figure 6:
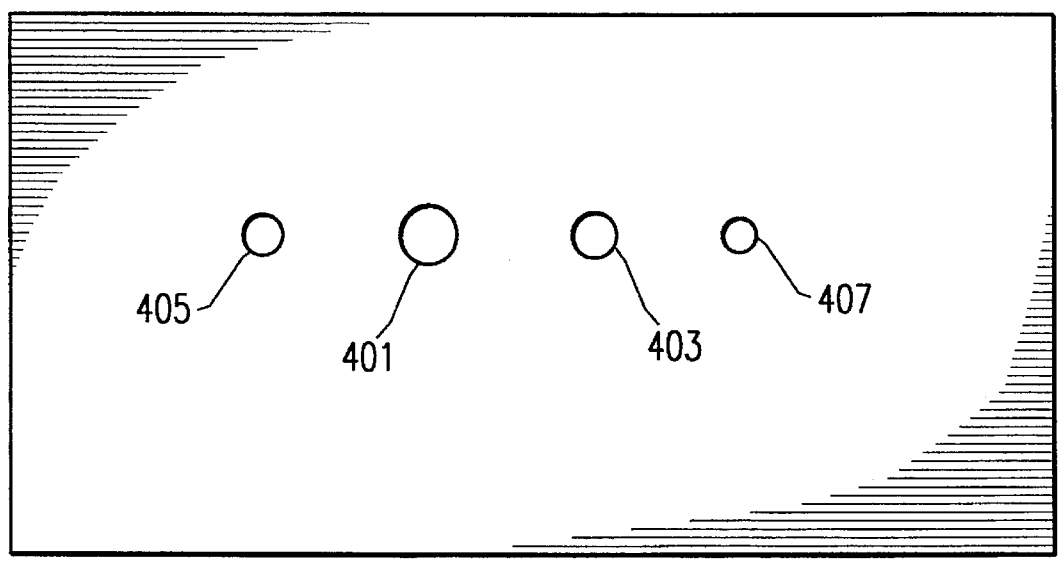

FIG. 5a illustrates a first input beam 209 and a second input beam 211, which constructively interfere to form a thermal grating, which then scatters the corresponding input beams 209, 211 to generate F-D4WM signal beams, 225, 303. Note that in the above description of the embodiment of the present invention, only one of the signal beams 225 was discussed, since only one such signal beam 225 is of practical interest. However in embodiments of the present invention in which fiber optic cables are used, both signal beams 225, 303 may be generated, summed and/or multiplied. Placing a screen behind the sample cell 221 allows four laser spots formed by the four beams 209, 211, 255, 303 to be observed. FIG. 6 is a photograph of the four laser spots formed by the illustrated embodiment the present invention. Two bright spots 401, 403 are due to the input beams 209, 211, and two smaller spots, 405, 407 are due to the signal beams 225, 303, respectively.

Figure 5B:
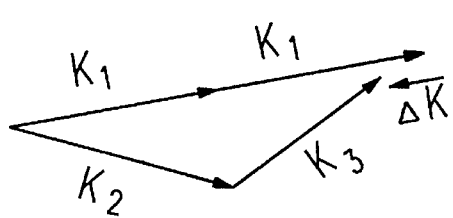
FIG. 5b illustrates the relationship between the input beams and the signal beams when the first input beam has a greater intensity then the second input beam.
Figure 5C:
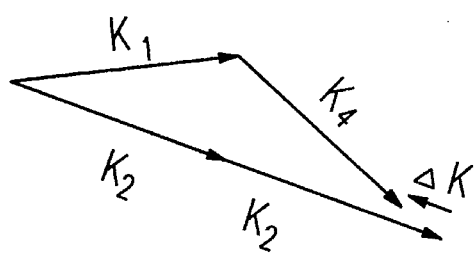
FIG. 5c illustrated the relationship between the input beams and the signal beams when the second input beam has a greater intensity then the first input beam.

When both input beams 209, 211 have the same intensity, two signal beams 225, 303 with the same intensity are observed. Such is the case illustrated in FIG. 5a. $K_1$, $K_2$, $K_3$, and $K_4$ represent the beam vector of four beams, 209, 211, 225, 303, respectively. If the intensity of the first input beam 209 is much stronger than that of the second input beam 211, the signal beam 225 is much stronger than the signal beam 303, as shown in FIG. 5b. Similarly, if the intensity of the second input beam 211 is much stronger than that of the first input beam 209, then the signal beam 303 is much stronger than the signal beam 225, as shown in FIG. 5c.

Generation of signal beams 225, 303 in a F-D4WM setup can be described in terms of dynamic holography. Constructive interference between the first input beam 209 and the second input beam 211 creates a dynamic grating with a period of P, where $P=\lambda/[2\sin(\Theta/2)]$, $\lambda$ is the laser wavelength, and $\theta$ is the angle between the two input beams. The signal beams, 225, 303 are then generated by the scattering of the input beams 209, 211, respectively, off the grating. As required in all nonlinear four-wave mixing processes, conservation of both energy and momentum must be satisfied in F-D4WM experiments for effective energy transfer. The energy conservation requires that $$\omega_3 = 2\omega_1 - \omega_2 = 2\omega - \omega = \omega \qquad (3)$$

and $$\omega_4 = 2\omega_2 - \omega_1 = 2\omega - \omega = \omega \qquad (4)$$

Since both incident beams 209, 211 have the same frequency, the signal beams 225, 303 also have the same frequency. Furthermore, momentum conservation requires that $$K_3 = 2K_1 - K_2 \qquad (5)$$

and $$K_4 = 2K_2 - K_1 \qquad (6)$$

Equations 5 and 6 indicate that the F-D4WM signal beam is most effectively generated in the $K_3$ and $K_4$ directions, as shown in FIG. 5b and 5c. Experimental results agree with Equations 5 and 6 as shown in FIG. 6.

Although only two input beams are used in the F-D4WM method of the present invention shown in FIG. 5b and 5c, they are still considered four-wave mixing methods, since the input beam 209 having the greater intensity provides two waves, the input beam 211 having the lesser intensity provides the third wave, and the signal beam 225 becomes the fourth wave, making the process a four-wave mixing method. The fact that the input beam having the greater intensity provides two waves accounts for the factor of two in equations 5 and 6. In FIG. 5b, the more powerful input beam 209 serves as the pump beam that consists of two forward waves, and the less powerful input beam 211 serves as the probe beam that generates the signal beam 225. Similarly in FIG. 5c, the more powerful input beam 211 serves as the pump beam that consists of two forward waves and the less powerful input beam 209 serves as the probe beam that generates the signal beam 303. $\Delta K$ represents vector difference between (1) the sum of the probe beam vector and the signal beam vector, and (2) twice the pump beam vector ($\Delta K = K_2 + K_3 - 2K_1$). $\Delta K$ is due to the angle between the pump and probe beams, the difference in the input wave arrival times or the difference in the input beam path length, and the ratio of the intensity of the pump beam to the intensity of the probe beam.

The signal beam 225 of the present invention can be enhanced by optimizing several parameters, including total laser intensity $I_t$. The efficiency of a F-D4WM grating, formed by the two input beams 209, 211 inside a nonlinear medium, such as a liquid analyte, is strongly affected by (1) the angle e between the two input beams, (2) the difference in input wave arrival times or the difference in input beam path length, and (3) the beam intensity ratio of the two input beams. Therefore, the angle $\Theta$ between the two input beams is preferably kept as small as possible in order to obtain optimum phase matching especially when using a thin sample cell 221. In the preferred embodiment of the present invention, the angle between the input beams 209, 211, is less than 1–5 degree. In addition, the smaller the angle $\theta$ between the two input beams 209, 211, the wider and sharper the F-D4WM grating period will be. A grating with a larger period is less vulnerable to grating washout due to thermal motion and external disturbance such as flow turbulence. Therefore, in accordance with the preferred embodiment of the present invention, better grating efficiency and higher signal strength can be expected with smaller angles $\Theta$ between the two input beams 209, 211. Furthermore, a smaller angle $\theta$ also increases the beam interaction volume and, hence, strengthens the F-D4WM signal. Therefore, in accordance with the preferred embodiment of the present invention, reducing the angle $\theta$ significantly increases the strength of the signal beam 225. When applying the present invention to detect concentrations of trace analytes, an angle as wide as 1.5° typical yields excellent detection limits. Therefore, optical alignment requirements are not severely restricted. Small-angle alignments are especially easy to perform in this two-input beam F-D4WM setup, since a single focusing lens is preferably used to focus all input beams 209, 211 instead of two or three lenses usually required in a three-input-beam D4WM method.

Another important parameter that could affect the grating sharpness is the difference between the path lengths or arrival times of the two input beams 209, 211. Optimum constructive interference between the two input coherent beams 209, 211 can be obtained in the preferred embodiment when the phase matching of the waves is at a maximum. Hence, it is preferable to keep the difference between the path lengths shorter than the laser coherence lengths ($L=c/\pi\Delta v$) in order to form sharp F-D4WM gratings. Many popular lasers offer sufficient room for convenient optical alignments and may be used in accordance with the present invention. For example, a simple argon ion laser has a relatively long coherence length (e.g., 5 cm) and more sophisticated narrow-bandwidth lasers, such as dye lasers, have much longer coherence length or coherence time.

The F-D4WM signal-to-noise ratio of the present invention can be optimized significantly in accordance with the preferred embodiment of the present invention by carefully adjusting the intensity distribution ratio for the two input beams 209, 211. In a F-D4WM setup where the signal beam 225 is monitored, as shown in FIG. 2a, a stronger signal beam 225 is obtained when the input beam 209 is stronger than the input beam 211, since the signal beam 225 is generated by first input beam 209 scattering off the thermal grating formed by the first input beam 209 and the second input beam 211. However, using a stronger first input beam 209 also increases the background noise due to the scattering of the beam 209 itself. Therefore, it is preferable to use an optimum intensity ratio $I_1:I_2$ of 7:3 for the input beam 209 in order to obtain both maximum signal strength and minimum background noise, where $I_1$ is the intensity of the input beam 209, and $I_2$ is the intensity of the input beam 211.

In accordance with the preferred embodiment of the present invention, to improve signal-to-noise ratio, background noise is suppressed by using an amplitude-modulated detection scheme. If the signal beam 225 is monitored as shown in FIG. 2a, most of the background noise comes from the scattering of the input beam 209. Therefore in the preferred embodiment of the present invention, the input beam 211 is modulated instead of the input beam 209 in order to obtain maximum noise suppression. Alternatively, if the signal beam 303 is monitored, the input beam 209 is modulated instead of the input beam 211, in order to obtain maximum suppression of noise originating most from the input beam 211.

Figure 7:
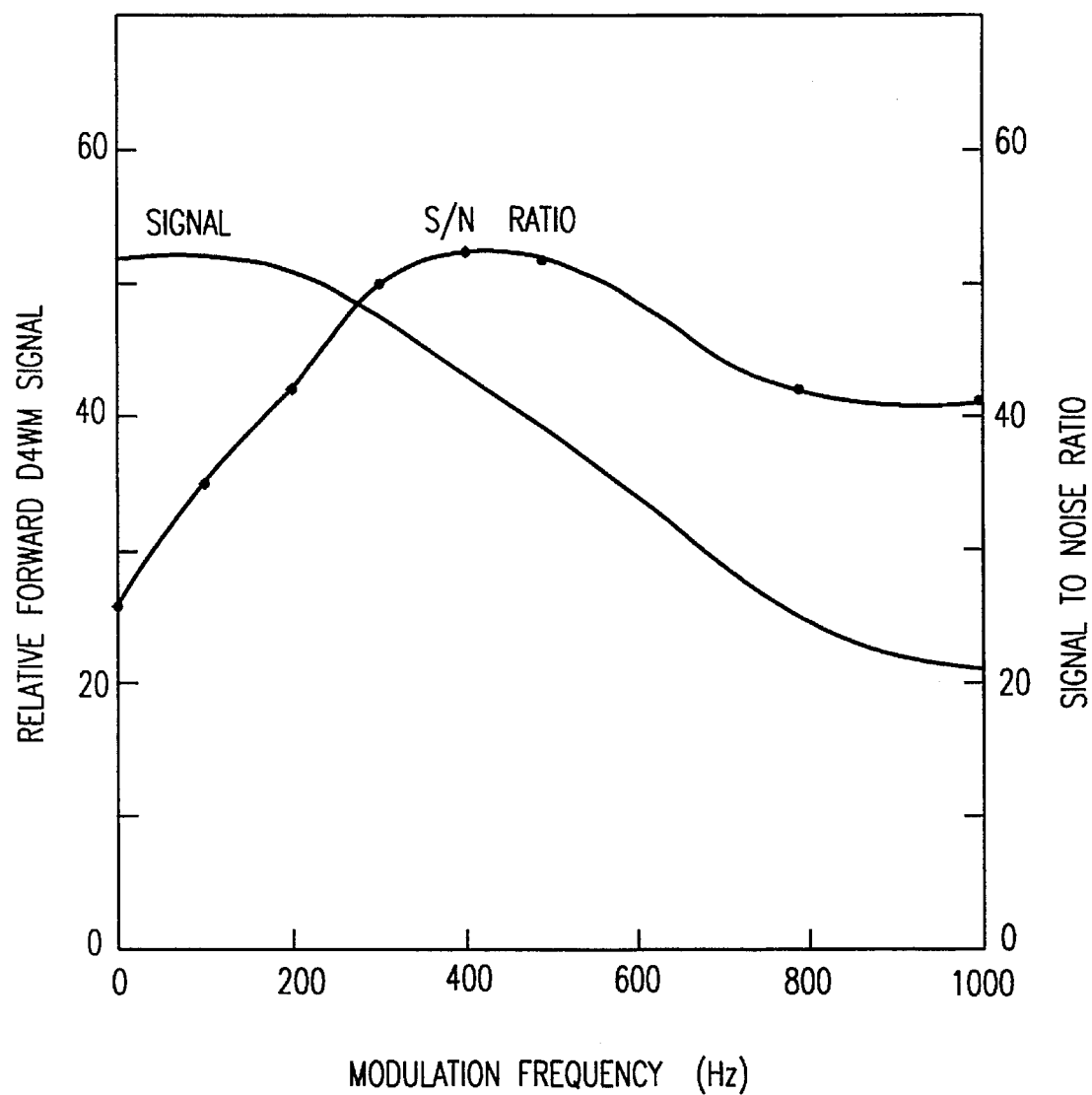
FIG. 7 illustrates the dependence of signal and signal-to-noise ratio on the chopper modulation frequency.

FIG. 7 illustrates the dependence of signal and signal-to-noise ratio on the chopper modulation frequency for one embodiment of the present invention analyzing one particular analyte. By amplitude modulating the input signal 211 at the correct frequency, sufficient time is allowed for the grating to form completely, and all other amplitude modulation frequencies, including amplitude modulation frequencies at the chopper frequency which are out of phase with the chopper, can be filtered out by the lock-in amplifier 238. A signal line 240 couples the amplitude modulation device 223' to the lock-in amplifier 238. Frequency and phase information are passed over the signal line 240. The intensity of the signal beam 225 remains strong at low modulation frequencies, since sufficient time is allowed between on and off cycles for the F-D4WM grating to form completely. The intensity of the signal beam 225 decreases slowly as the modulation frequency is increased, since less time is available to form a complete and sharp grating. On the other hand, the background noise is suppressed to a greater degree by the lock-in amplifier 238 at higher modulation frequencies. Although the signal is weaker at higher modulation frequencies, the signal-to-noise ratio remains reasonably high and stable at higher frequencies. Hence, the present invention offers a wide usable modulation frequency range. The particular range will vary dependent upon the analyte. Alternatively, the amplitude of both the signal beams 225, 303 could be monitored and common mode noise subtracted by known techniques.

Although there are similar features between degenerate four-wave mixing methods and holography (or holography-like spectroscopic methods relying on two-color pumped-probed thermal gratings), the two processes are not identical. While holography is a sequential process where recording and reconstruction (writing and reading) steps are separate (or time delayed), these steps occur simultaneously in a degenerate four-wave mixing experiment. Therefore, while only two photons need to exist simultaneously in holography, four photons must exist simultaneously in four-wave mixing methods. Another distinctive difference between holography and four-wave mixing is the different types of diffraction gratings generated. While only spatial diffraction gratings are involved in holography, both spatial diffraction gratings and temporal diffraction gratings could be used in four-wave mixing. The B-D4WM complex signal vector amplitude can be described as $P^3 \propto (Ae_b e_p^* \cdot e_f + Be_f e_p^* \cdot e_b + Ce_p^* e_f e_b)E_f E_b E_p^*$, where A, B, and C are constants depending on the nonlinear susceptibility of the analyte and $e_f$, $e_b$, $e_p$ are polarization-state vectors of the forward, backward, and probe beams, respectively. In the equation above, the first and second terms describe contributions from the volume gratings formed by forward-probe and backward-probe beam pairs, respectively. These two terms can be used also to describe processes in holography. However, the third term describes contribution from the temporal grating (i.e., coherent gratings), and this grating is characteristic of B-D4WM. Another important and useful characteristic property of both forward- and backward-scattering four-wave mixing methods is the phase-conjugate property of the signal beam. The phase-conjugate property in the illustrated forward-scattering D4WM signal beam is verified by placing a thin wire in the probe beam path and observing its image on a white screen that is positioned in the signal beam path. The image of the object (i.e., a wire or anything small that can be placed inside the probe beam path) is "carried" and projected very clearly on the screen by the phase-conjugate signal beam when the distance between the image screen and the nonlinear medium (i.e., analyte cell) is the same as the distance between the object and the analyte cell. The phase-conjugate property of the signal beam generated by the analyte (i.e., the nonlinear medium) in a D4WM method has many potential applications including autocorrection of beam distortion or optical aberration.

The use of a single short-focal length lens for all the input beams not only simplifies focusing and mixing simultaneously, it also maximizes photon density available at the sample cell significantly, and hence, allows the use of low-power (milliwatts or less) lasers in a nonlinear spectroscopic method. In the illustrated two-beam F-D4WM setup, the signal beam 225 is still strong even when laser power as low as 5 mW is used. Tight focusing and compact wave mixing available with the inventive two-beam F-D4WM configuration reduces the laser power requirements sufficiently to allow lowcost lasers, such as He-Ne lasers or diode lasers, to be used as excitation light sources in the present invention. Furthermore, because the beam spots of the input beams 209, 211 are very compact, the present invention may be directly interfaced to known HPCE, HPLC, and atomizer systems such that the laser mixing can be accomplished directly in the capillary tube or column (i.e., the capillary tube or column is the sample cell).

The present invention provides an ultrasensitive detection method for analytes in any physical state (e.g., liquid, gas, or solid) using laser powers at the milliwatt range. Since only two input laser beams are involved in this four-wave mixing process, the optical alignment is much easier than other four-wave mixing methods, no critical optical alignment constraints exist, and the beam spots are easily focused to a sufficiently small volume to allow detection directly with an HPCE, HPLC, or gas-phase atomizer setup. Improved sub-attomole detection sensitivity, picoliter probe volume, simple one-laser one-wavelength setup, and convenient analyte introduction make the present invention applicable to may problems, including relatively inexpensive, simple, ultrasensitive detection for use in HPCE, HPLC, or gas-phase atomizer systems. The laser power requirement for producing a strong F-D4WM signal is unusually low (milliwatt or less) compared to conventional backward-D4WM experiments. Furthermore, in accordance with the present invention, simple diode lasers may be used in place of larger, more expensive lasers, such as argon-ion lasers.

In one embodiment of the present invention, a preliminary F-D4WM detection limit of $7.1 \times 10^{-9}$M (S/N=2) for eosin B is determined using a 0.1-mm-thick sample cell and a total argon ion laser power of 0.5 W. This corresponds to a mass detection limit of $7 \times 10^{-19}$ mol of eosin B within a detection probe volume of 98 pL. Using the same F-D4WM setup, a detection limit of $4.6 \times 10^{-7}$M or $45 \times 10^{-18}$ mol for iodine in $CCl_4$ is also determined.

Table 1 compares the results of the present invention to four-wave mixing laser spectroscope methods using different configurations. The present invention requires a much simpler optical setup and a much lower laser power and yet yields comparable detection limits as compared to backward-scattering D4WM methods. When compared to a B-D4WM method using a pulsed excimer-pumped dye laser, the present invention yields an iodine mass detection limit that is 351 times better, and does not require a more expensive dye laser. When compared to a laser-induced thermal diffraction method using both an argon ion laser and a He-Ne laser, the present invention yields an iodine concentration detection limit that is 1.8 times better (and an iodine mass detection limit that is 3067 times better), and yet it employs a simpler optical setup with only a single laser instead of two different lasers. Thus, the present invention is easier to use and less expensive.

Conclusion

A two-input beam F-D4WM optical setup offers several advantages as a novel nonlinear laser spectroscopic method. Compared to backward-scattering D4WM and other four-wave mixing methods, where three input beams are used, the optical alignment of a two-beam F-D4WM method is significantly easier. For example, in a "boxcar" F-D4WM configuration, where two pump beams and one probe beam are required, the optical alignment is not as simple. Since only two input laser beams 209, 211 are used and the signal beam 225 is visible to the naked eye, the optical alignment of this nonlinear F-D4WM laser system in accordance with the present inventive method is relatively simple, even when compared to many conventional one-beam or two-beam laser methods. In addition, a single lens may be used to focus all input beams. Furthermore, a single lens may be used to mix all input beams. Still further, in accordance with one embodiment of the present invention, fiber optic cables are used to further simplify alignment. Use of fiber optic cables to simplify the alignment of a D4WM detection system may be used with both backward and forward-scattering D4WM systems. Since the alignment of the present invention is simplified, the setup has a stable optical alignment. Therefore, there is little or no need to realign the system at regular relatively short intervals. Also, the two-wave input beam embodiment of the present invention has high wave-mixing efficiency inside a small volume with single short-focal-length focusing.

In addition, the efficiency of three beam wave-mixing methods strongly depends on the angle of the probe beam relative to the thermal grating for Bragg scattering condition, although the effect of the angle between the two pump beams is negligible.

Furthermore, these three input beams must be perfectly overlapped in order to obtain maximum wave-mixing efficiency, and hence, optical alignment is more complicated for a "boxcar" F-D4WM method as compared to that for a two-beam F-D4WM method.

In addition to simpler input beam alignments, it is also easier to mix waves with high efficiency in a two-beam F-D4WM method, since only a single lens is needed to focus and mix the input beams as shown in FIG. 2a (instead of two or three lenses needed in a B-D4WM method). Hence, it is relatively easy to use microsample cells or many popular small-diameter capillary flow cells for a two-beam F-D4WM detector. In the illustrated two-beam F-D4WM setup, the diameter of the focused beam spots at the sample cell is 34 µm or less, and hence, the laser probe volume inside the sample cell is 98 pL or less. Therefore, this F-D4WM detection method has many potential applications as an ultrasensitive detector for both fluorescing and non-fluorescing analytes for a capillary chromatography system or a capillary electrophoresis system. As indicated in equation 2, the F-D4WM signal has a cubic dependence on total input laser intensity, and hence, the signal could be enhanced significantly by increasing the input intensity. Therefore, the present invention has low laser power requirements due to the high wave mixing efficiency and high photon density available by tight focusing using a short focal-length lens. Since the laser power requirements are low, and the input beams are refocused, the present invention may take advantage of inexpensive light sources, such as diode lasers. Also, the present invention is compact and portable.

The D4WM detection method of the present invention is suitable for ultrasensitive analytical measurements, since they can yield sub-attomole mass detection sensitivity and they are capable of detecting both fluorescing and nonfluorescing analytes.

A number of embodiments of the present invention have been described. Nevertheless, it will be understood that various modifications may be made without departing from the spirit and scope of the invention. For example, the present invention may be used as a component part of any chemical analysis instrument system in which it is desired to detect the atomic or molecular absorption of a substance. For example the present invention may be used with any chemical separation instrument including liquid and gas chromatography HPCE and any optical spectrometry method in which the signal is based on absorption of light by the analyte. Furthermore, the present invention may employ any coherent light source capable of 1 milliwatt or less. Still further, the illustrated embodiments of the present invention are described as having an amplitude modulation device. In an alternative embodiment, the present invention may use a two channel detect and subtract method by which intensity variations or noise that are common each input beam are detected and subtracted from the signal beam. However, embodiments which have no such amplitude modulation or other signal to noise enhancement device are within the scope of the present invention. Furthermore, the present invention may be used with any combination of beam splitters, reflectors, lens, apertures, and other standard components of a laser or optical system, in order to accomplish the illustrated two input beam F-D4WM, or when used with fiber optic cables to direct beams of laser light, in order to accomplish the illustrated three beam B-D4WM. Accordingly, it is to be understood that the invention is not to be limited by the specific illustrated embodiment, but only by the scope of the appended claims.

I claim:

1. An apparatus for performing two-input-beam forward-scattering degenerate four-wave mixing for use in detecting absorption of light by an analyte, including:

(a) a sample cell for containing an analyte; and
   (b) a coherent light source having a coherence length, the coherent light source for generating a first and a second input coherent beam, each having respective incident paths and a path length from the coherent light source to the sample cell, the first input coherent beam path length minus the second input coherent beam path length being less than or equal to the coherence length of the coherent light source, the coherent light source being configured such that the first and second input coherent beams intersect within the analyte at an angle θ of less than approximately 5 degrees so as to generate a first and a second signal beam each having a collimated coherent beam generated by interaction of at least one of the first and second input coherent beams with a thermally induced refractive index grating formed by constructive interference of the first and second input coherent beams, the first and second signal beams having respective signal paths, the signal path of the first signal beam being at an angle from the incident path of the second input coherent beam approximately equal to θ, and the signal path of the second signal beam being at an angle from the incident path of the first input coherent beam approximately equal to σ; and
   (c) a detector disposed within the signal path of at least one signal beam, for receiving the coherent beam of such signal beam and determining from such signal beam absorption of light by the analyte in the sample cell.

2. The apparatus of claim 1, further including at least one lens through which each input coherent beam passes for focusing each input coherent beam to a single point within the sample cell.

3. The apparatus of claim 1, further including at least a first lens through which the first input coherent beam passes and a second lens through which the second input coherent beam passes, each lens having a common focal point, the common focal point being within the sample cell.

4. The apparatus of claim 1, wherein a ratio of the intensity of the first input coherent beam to the intensity of the second input coherent beam is approximately 7:3.

5. The apparatus of claim 1, further including an amplitude modulation device, disposed within the path of the second input coherent beam between the coherent light source and the sample cell for amplitude modulating the intensity of the second input coherent beam.

6. The apparatus of claim 5, wherein the amplitude modulation device is a solid state electronic light intensity modulation device.

7. The apparatus of claim 5, wherein the amplitude modulation device is a mechanical chopper.

8. The apparatus of claim 1, further including a first beam splitter for dividing the output of the coherent light source into the first input coherent beam and the second input coherent beam.

9. The apparatus of claim 8, further including:

(a) a first reflector disposed between the coherent light source and the first beam splitter;
   (b) a second reflector for redirecting the first input coherent beam toward a lens;
   (c) a third reflector for redirecting the second input coherent beam, such that the second input coherent beam propagates along a path that is approximately parallel to the path of the first input coherent beam between the beam splitter and the second reflector;

(d) a fourth reflector for redirecting the second input coherent beam toward the lens.

10. The apparatus of claim 1, further including:
   (a) at least one lens; and
   (b) a fiber optic cable;
wherein the output of the coherent light source is coupled to the fiber optic cable, the fiber optic cable being divided into two sections, the first section of cable for transmitting the first input coherent beam to a lens, the second section of cable for transmitting the second input coherent beam to a lens.

11. The apparatus of claim 10, wherein the lens to which the first input coherent beam is transmitted is at an end of the first section of fiber optic cable, and the lens to which the second input coherent beam is transmitted is at an end of the second section of fiber optic cable.

12. The apparatus of claim 11, further including:
   (a) an amplitude modulation device for amplitude modulating the intensity of the second input coherent beam; and
   (b) a fiber optic cable, coupled to the output of the coherent light source, and divided into two sections, the first section of cable for transmitting the first input coherent beam to the lens, the second section of cable for transmitting the second input coherent beam to the amplitude modulation device.

13. The apparatus of claim 11, further including a second lens, wherein the first signal beam and the second signal beam are summed within the second lens.

14. The apparatus of claim 11, further including:
   (a) an aperture disposed within the signal path of the first signal beam for reducing background noise;
   (b) a lens disposed within the signal path of the first signal beam for focusing the first signal beam;
   (c) a filter disposed within the signal path of the first signal beam for attenuating light having a wavelength other the wavelength of the light emitted by the coherent light source; and
   (d) a detector disposed within the signal path of the first signal beam for receiving the coherent beam of such first signal beam and converting the coherent beam of such first signal beam into an electrical signal.

15. The apparatus of claim 14, wherein the detector is a photomultiplier tube.

16. The apparatus of claim 14, further including an amplifier for amplifying the electrical output of the detector.

17. The apparatus of claim 16, wherein the gain of the amplifier is frequency dependent, and the gain is greatest at the amplitude modulation frequency.

18. The apparatus of claim 1, wherein the sample cell is a capillary tube of a high power/high performance capillary electrophoresis system.

19. The apparatus of claim 1, wherein the sample cell is a column of a high performance liquid chromatography system.

20. The apparatus of claim 1, further including a detection device disposed in the signal path of the first signal beam for detecting the intensity of the first signal beam.

21. The apparatus of claim 20, wherein the detection device includes a photomultiplier tube.

22. The apparatus of claim 21, further including a line filter for attenuating light at wavelengths other than approximately a wavelength of the coherent light source, disposed between the sample cell and the photomultiplier tube.

23. The apparatus of claim 22, further including a beam trap disposed with respect to the sample cell such that the first and second input coherent beams are trapped after passing through the sample cell.

24. The apparatus of claim 20, further including an aperture disposed between the sample cell and the detection device for reducing background noise.

25. The apparatus of claim 20, further including an amplifier coupled to the detection device for amplifying an electrical output of the detection device.

26. The apparatus of claim 25, further including an amplitude modulation device disposed in the incident path of the second input coherent beam between the coherent light source and the sample cell, wherein the gain of the amplifier is frequency dependent and is greatest at the modulation frequency of the amplitude modulation device.

27. The apparatus of claim 1, wherein the sample cell is coupled to a source of the analyte and a sink for the analyte, such that the analyte flows through the sample cell.

28. The apparatus of claim 27, further including a pump coupled to the sample cell for causing the analyte to flow through the sample cell.

29. The apparatus of claim 1, wherein the coherent light source is a diode laser.

30. The apparatus of claim 1, wherein beam spots for the first and the second input coherent beams within the analyte are less than 34 µm.

31. The apparatus of claim 1, wherein the intersecting angle of the first and second input coherent beams is in the range of 0.5 to 1 degree.

32. An apparatus for performing three-input-beam backward degenerate four-wave mixing for use in detecting atomic absorption of light by an analyte, including:
   (a) a coherent light source;
   (b) a beam splitter;
   (c) a lens;
   (d) a sample cell for containing an analyte; and
   (e) a fiber optic cable divided into three sections for dividing an output of the coherent light source into three input beams, the first section of fiber optic cable for directing the first input beam to strike a first side of the sample cell, the second section of fiber optic cable for directing the second input beam to strike a second side of the sample, cell opposite the first side, and the third section of fiber optic cable for directing the third input beam to pass through the beam splitter and the lens, and to intersect the first and second input beams at a point within the sample cell;
whereby a phase conjugate signal beam is generated within the analyte in response to constructive interference between the first and second input beams, and the signal beam reflects off the beam splitter.

33. The apparatus of claim 32, further including a detector for detecting the intensity of the signal beam, disposed to receive the signal beam reflected off the beam splitter.

34. The apparatus of claim 33, wherein the detector includes a photomultiplier tube.

35. The apparatus of claim 34, further including an amplifier coupled to the detector for amplifying the output of the detector.

36. The apparatus of claim 35, further including an amplitude modulation device disposed within the path of the third input signal.

37. The apparatus of claim 36, wherein the gain of the amplifier is frequency dependent, and the greatest gain is provided at frequencies near the modulation frequency of the modulation device.

38. The apparatus of claim 36, wherein the amplifier is coupled to a processor for digitizing, recording, and processing the output of the amplifier.

* * * * *